US011514068B1

(12) United States Patent
Frakes et al.

(10) Patent No.: US 11,514,068 B1
(45) Date of Patent: *Nov. 29, 2022

(54) DATA VALIDATION SYSTEM

(71) Applicant: Lumeris Solutions Company, LLC, Maryland Heights, MO (US)

(72) Inventors: Jason Frakes, Maryland Heights, MO (US); Marcus Stucke, Maryland Heights, MO (US); Ian Erlandson, Maryland Heights, MO (US)

(73) Assignee: LUMERIS SOLUTIONS COMPANY, LLC, Maryland Heights, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/565,660

(22) Filed: Dec. 30, 2021

Related U.S. Application Data

(63) Continuation of application No. 16/723,444, filed on Dec. 20, 2019, now Pat. No. 11,243,972.

(60) Provisional application No. 62/785,972, filed on Dec. 28, 2018.

(51) Int. Cl.
| | |
|---|---|
| *G06F 16/00* | (2019.01) |
| *G06F 16/25* | (2019.01) |
| *G16H 10/60* | (2018.01) |
| *G06F 17/18* | (2006.01) |
| *G06F 16/248* | (2019.01) |

(52) U.S. Cl.
CPC ......... *G06F 16/252* (2019.01); *G06F 16/248* (2019.01); *G06F 17/18* (2013.01); *G16H 10/60* (2018.01)

(58) Field of Classification Search
CPC ...... G06F 16/252; G06F 16/248; G06F 17/18; G16H 10/60
See application file for complete search history.

(56) References Cited

U.S. PATENT DOCUMENTS

| | | | |
|---|---|---|---|
| 7,315,826 B1 * | 1/2008 | Guheen | G06Q 30/0201 705/7.29 |
| 8,924,269 B2 * | 12/2014 | Seubert | G06Q 40/00 705/35 |
| 10,248,508 B1 * | 4/2019 | Park | G06F 11/0751 |
| 2006/0015405 A1 * | 1/2006 | Bala | H04N 21/44224 705/14.69 |
| 2012/0254832 A1 * | 10/2012 | Aman | G06F 16/24 717/109 |

(Continued)

*Primary Examiner* — Noosha Arjomandi
(74) *Attorney, Agent, or Firm* — Christopher R. Carroll; The Small Patent Law Group LLC

(57) ABSTRACT

A validation system and method are provided that examine data for use in tracking and/or generating an action plan. Data is received and stored at an implementation data store from production data sources. Evaluation rules are applied to the data by a data storage system. The evaluation rules are applied by running previously created scripts of commands of the data storage system. Applying the evaluation rules to the one or more sets of the data outputs a deviation measure for at least one of the sets of the data. The deviation measure and a restricted list of defined validation decisions is presented to an analyst for the data. A selected validation decision is received, and the data is validated for use in the action plan, rejected for use in the action plan, or identified as requiring additional analysis before being validated for use in the action plan.

20 Claims, 8 Drawing Sheets

(56) References Cited

U.S. PATENT DOCUMENTS

| | | | | |
|---|---|---|---|---|
| 2012/0259722 | A1* | 10/2012 | Mikurak | G06Q 30/0261 |
| | | | | 705/26.1 |
| 2014/0108357 | A1* | 4/2014 | Procops | G06F 40/18 |
| | | | | 707/690 |
| 2016/0299936 | A1* | 10/2016 | Chavda | G06F 16/958 |
| 2017/0180322 | A1* | 6/2017 | Agarwal | H04L 63/0263 |
| 2018/0096020 | A1* | 4/2018 | Sreenivasa | G06F 16/958 |
| 2019/0244675 | A1* | 8/2019 | Meiri | G11C 29/38 |
| 2020/0042924 | A1* | 2/2020 | Muraoka | G06Q 10/10 |
| 2020/0073743 | A1* | 3/2020 | Lisuk | G06Q 10/10 |
| 2020/0210401 | A1* | 7/2020 | Swami | G06F 16/215 |
| 2020/0263995 | A1* | 8/2020 | Gaal | G08G 1/0129 |
| 2020/0311680 | A1* | 10/2020 | Wahl | H04L 51/56 |
| 2020/0410614 | A1* | 12/2020 | Bonageri | G06N 20/20 |
| 2021/0350923 | A1* | 11/2021 | McKirdy | G06K 7/1413 |

\* cited by examiner

| Data Operations | | | |
|---|---|---|---|
| Client | | Date | 11/02/2018 |
| Complete Task | | Completed By | Task Result |
| ✓ File Load Monitoring Report | | | Pass |
| ✓ Data Load Report | | | Pass |
| ✓ Ipaas Load Message Error Report | | | Pass |
| ✓ QC - Claims (Consult 01) | | | Pass |
| ✓ QC - Claims (Post ODS) | | | Pass |
| ✓ QC - CMS (Consult01) | | | Pass |
| ✓ QC - CMS (Post ODS) | | | Pass |
| ⊘ QC - EMPI (Post Completion) | | One or more tests has returned zero records | |
| ✓ OC - EMPI(Post ODS) | | | Pass |
| ✓ QC - Integrity (Consult01) | | | Pass |

FIG. 4

| Member Demographics | | | |
|---|---|---|---|
| Age | Male | Female | Unknown |
| 20-29 | 130 | 142 | 0 |
| 30-39 | 640 | 669 | 0 |
| 40-49 | 1561 | 1546 | 0 |
| 50-59 | 3988 | 3862 | 0 |
| 60-69 | 8575 | 10708 | 0 |
| 70-79 | 18358 | 24260 | 0 |
| 80-89 | 7565 | 12423 | 0 |
| 90-99 | 1038 | 2565 | 0 |
| Showing 1 of 8 of 8 entries | | | |

FIG. 5

LoadErrorMsgChecks-Member
Error message checks for Member files over the last 26 loads, with 2 std dev tolerance

| Within Std Dev | Record_Count | AvgErrorCnt | StDevErrorCnt | Logical_File_Nm | File_Submit_Grp_Id | Load_Dt | Edit_Proc_Nm | Message_Txt |
|---|---|---|---|---|---|---|---|---|
| Y | 0 | 0.02 | 0.15 | Member | 9990003131 | 12/19/2018 7:17:13 AM | No Edit Errors | Last Load was Completely Successful |
| Y | 0 | 68.28 | 140.11 | Member | 9990003131 | 12/19/2018 7:17:13 AM | No Edit Errors | Last Load was Completely Successful |
| Y | 0 | 0.12 | 0.47 | Member | 9990003131 | 12/19/2018 7:17:13 AM | No Edit Errors | Last Load was Completely Successful |
| Y | 0 | 0.24 | 0.95 | Member | 9990003131 | 12/19/2018 7:17:13 AM | No Edit Errors | Last Load was Completely Successful |

FIG. 11

DATA VALIDATION SYSTEM

CROSS-REFERENCE TO RELATED APPLICATIONS

This application is a continuation of U.S. patent application Ser. No. 16/723,444 (filed 20 Dec. 2019), which claims priority to U.S. Provisional Application No. 62/785,972 (filed 28 Dec. 2018). The entire disclosures of these applications are incorporated herein by reference.

FIELD

Embodiments of the subject matter described herein relate to computerized systems that validate data received from one or more production sources for use in action plans for entities.

BACKGROUND

Data can be obtained from a variety of sources and used to determine historical events related to entities associated with the data, current statuses of the entities, and/or for generating action plans for the entities. For example, medical data can be obtained for persons that represents previous healthcare events of those persons. This medical data can be used to determine whether a recommended healthcare plan is being followed for a person and/or to create a new or updated health care plan.

That data that is obtained can be provided in different forms, can be provided from different sources, can be created or entered by different persons, or the like. This can result in the data significantly varying, even in situations where varying data is intended to represent the same type of events. Variances in the data can prevent the data from being efficiently examined and compared with each other to compare with an action plan or create an action plan.

Currently, variances in the data may require persons having extensive knowledge and/or training to identify the data variances and/or fix the data variances. In situations where large volumes of data are examined for variances, this can result in a significant amount of work for such highly knowledgeable and trained persons. This can significantly reduce the efficiency at which the data is examined and/or action plans are created and can significantly increase the financial costs involved in having enough educated and highly trained persons to perform the examination and/or resolution of the data variances.

BRIEF DESCRIPTION

One embodiment of the inventive subject matter described herein provides a method for validating data for use in one or more of tracking or generating an action plan. The method includes receiving the data at an implementation data store from one or more production data sources via one or more computerized communication networks, storing the data in the implementation data store using a data storage system, and applying evaluation rules to one or more sets of the data in the implementation data store. The evaluation rules are used to evaluate the data against one or more designated expectations to determine whether the data deviates from or has exceptions to the designated expectations. The evaluation rules can be applied to the one or more sets of the data by running previously created scripts of commands of the data storage system. Applying the evaluation rules to the one or more sets of the data outputs a deviation measure for at least one of the sets of the data. The method also includes presenting, to an analyst, the deviation measure and a restricted list of defined validation decisions for the one or more sets of the data, receiving a selected validation decision in the restricted list from the analyst, and one or more of validating the one or more sets of the data for use in the action plan, rejecting the one or more sets of the data for use in the action plan, and/or identifying the one or more sets of the data as requiring additional analysis before validating the one or more sets of the data for use in the action plan.

In one embodiment, a data validation system that validates data for use in one or more of tracking or generating an action plan for at least one person is provided. The data validation system includes an implementation data store configured to receive the data from one or more production data sources via one or more computerized communication networks, and one or more processors configured to direct the implementation data store to store the data using a data storage system. The one or more processors are configured to apply evaluation rules to one or more sets of the data in the implementation data store. The evaluation rules are applied to the one or more sets of the data by the one or more processors running previously created scripts of commands of the management system. The one or more processors are configured to determine a deviation measure for at least one of the sets of the data based on the evaluation rules applied to the one or more sets of the data. The one or more processors are configured to present the deviation measure and a restricted list of defined validation decisions for the one or more sets of the data to the analyst. The one or more processors also are configured to receive a selected validation decision in the restricted list from the analyst. The one or more processors also are configured to one or more of validate the one or more sets of the data for use in the action plan, reject the one or more sets of the data for use in the action plan, or identify the one or more sets of the data as requiring additional analysis before validating the one or more sets of the data for use in the action plan.

In one embodiment, a tangible and non-transitory computer readable storage medium is provided that includes one or more sets of instructions. This storage medium can be represented by one or more of the scripts described above. These instructions can be implemented using one or more processors to direct the one or more processors to receive data at an implementation data store from one or more production data sources via one or more computerized communication networks, direct storage of the data in the implementation data store using a data storage system, and apply applying evaluation rules to one or more sets of the data in the implementation data store. The evaluation rules are applied to the one or more sets of the data by running previously created scripts of commands of the data storage system. Applying the evaluation rules to the one or more sets of the data outputs a deviation measure for at least one of the sets of the data. The instructions also direct the processor(s) to direct presentation of the deviation measure to an analyst of the deviation measure and a restricted list of defined validation decisions for the one or more sets of the data, receive a selected validation decision in the restricted list from the analyst, and one or more of validate the one or more sets of the data for use in the action plan, reject the one or more sets of the data for use in the action plan, or identify the one or more sets of the data as requiring additional analysis before validating the one or more sets of the data for use in the action plan.

BRIEF DESCRIPTION OF THE DRAWINGS

The subject matter described herein will be better understood from reading the following description of non-limiting embodiments, with reference to the attached drawings, wherein below:

FIG. 4 illustrates part of another GUI displaying deviation measures on one or more of the user devices shown in FIG. 1;

FIG. 5 illustrates part of another GUI that displays deviation measures on one or more of the user devices shown in FIG. 1;

FIG. 11 illustrates another GUI that displays a deviation measure on one or more of the user devices shown in FIG. 1.

DETAILED DESCRIPTION

Figure 1:
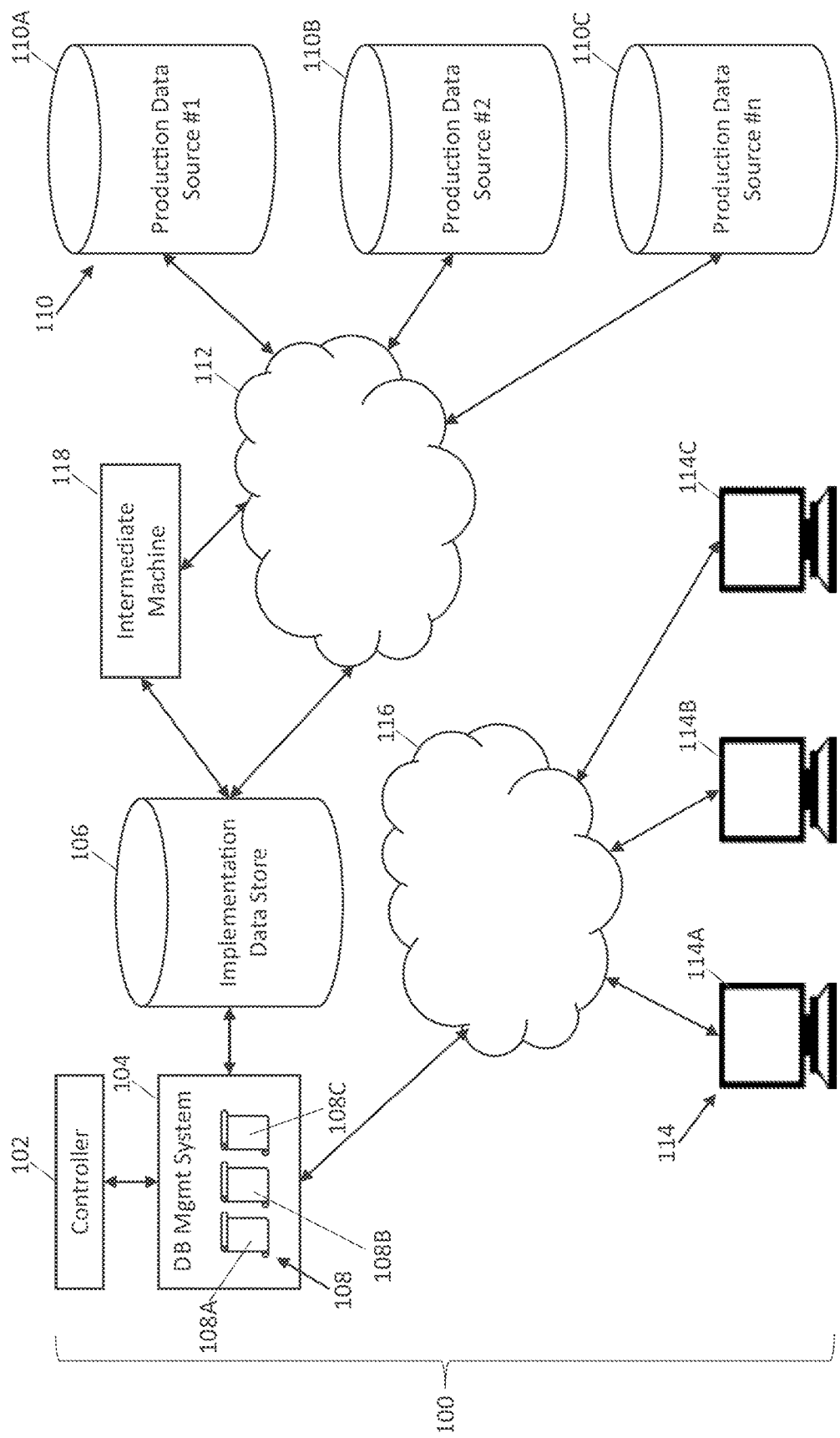
FIG. 1 schematically illustrates one embodiment of a data validation system.

Embodiments of the subject matter disclosed herein describe data validation systems and methods that examine and validate data used to track and/or generate an action plan. The data is received at a data store from one or more data sources, and one or more evaluation rules are applied to one or more sets of the data. The evaluation rules are used to evaluate the data against one or more designated expectations to determine whether the data deviates from or has exceptions to the designated expectations. These evaluation rules can be applied by automatically and/or manually initiating previously created software scripts of computer commands of a data storage system to the set(s) of data. The output of these evaluation rules can be one or more deviation measures of how the data varies from a baseline or expected value, or from a statistical measure of the data in the set(s). The deviation measure can be presented to a lower-level analyst and can indicate whether the data is validated (e.g., whether the data is legitimate). The data may not be validated if the deviation measure indicates that errors (e.g., input errors, collection errors, or the like) cause the information represented by at least some portions of the data to be incorrect or more likely than not to be incorrect, or at least not represent actual or true information about the entity (e.g., person) associated with the data.

As one example, some data input entities may populate a field of a table with a default value when this field is rarely used by those input entities. But, the contents of this field in the table may be used to track and/or generate an action plan. As a result, the default value can cause the status of the action plan to be incorrectly tracked and/or an erroneous action plan to be generated. Application of the evaluation rule(s) to the data to yield a deviation measure can indicate whether the data is validated (e.g., the data appears to be legitimately entered with the contents of the data being intentionally set to values believed to be accurate) or invalid (e.g., the data appears to be incorrectly entered with the data contents being unintentionally set to values that are not believed to be accurate).

A defined list of validation decisions also can be presented to the analyst. The analyst can select at least one of the validation decisions based on the deviation measure, and the system can validate the data for use in tracking and/or generating an action plan based on the selected validation decision, reject the data from being used in tracking and/or generating an action plan based on the selected validation decision, and/or identify at least part of the data as requiring additional analysis before validating or rejecting the data for use in the action plan.

At least one technical effect of the validation system and method described herein is to solve the big-data problem of quickly validating data that may or may not accurately reflect the information intended to be represented by the data. To ensure that all relevant data is captured for a wide variety of entities, the data may potentially represent a wide variety of information about the different entities. But, because of errors inputting the information, using default or nil values for data entries that are rarely used, and other data input errors, at least some of the data can be detrimental to forming and/or tracking an action plan based on the data. Experienced and/or highly trained operators may be required to identify and/or fix the problems with the data. One or more embodiments of the subject matter described herein reduce the need for high level operator assistance in validating the data, and instead simplifies the validation process so that less experiences and/or less trained operators can validate (or reject) the data.

FIG. 1 schematically illustrates one embodiment of a data validation system 100. The data validation system 100 includes a controller 102 representing hardware circuitry that includes and/or is connected with one or more processors. A processor can be a combination of one or more microprocessors, one or more integrated circuits, and/or one or more field programmable gate arrays, or other electronic logic-based devices. The controller 102 performs the operations described herein in connection with the controller 102.

The controller 102 communicates with a data storage system 104 ("Data System" in FIG. 1) to direct validation analysis of data stored in an implementation data store 106. The data storage system 104 represents hardware circuitry that includes and/or is connected with one or more processors that operate under the direction of one or more software scripts or programs 108 (e.g., scripts 108A-C in FIG. 1) to manage data stored in the implementation data store 106. The implementation data store 106 can represent one or more databases or other tangible and non-transitory computer-readable storage media (e.g., one or more computer servers, computer hard drives, removable drives, optical disks, solid state memories, magnetic disks, or the like).

The controller 102, data storage system 104, and the implementation data store 106 are shown in FIG. 1 as being separate components of the data validation system 100. Alternatively, two or all the controller 102, data storage system 104, and/or implementation data store 106 can be combined into a single component of the system 100. For example, the same hardware circuitry and associated software can perform the operations of the controller 102, the data storage system 104, and/or the implementation data store 106.

The data storage system 104 can represent one or more systems that receive, store, and control access to data stored in one or more computer-readable storage media (which also can be represented by the data storage system 104). In one embodiment, the data storage system 104 is one or more databases. For example, the data storage system 104 can be a relational database management system. Alternatively, the data storage system 104 can be a flat database system, an object-oriented database system, a hierarchical database system, a document storage system, or an object database system. Examples of data storage systems include MySQL, SQL server, Oracle, dBASE, and FoxPro. Another example of such a data storage system 104 is a hierarchical database, such as MongoDB.

The scripts 108 can direct the data storage system 104 to load, retrieve, modify, analyze, or perform other actions, on the data stored in the implementation data store 106, as described herein. The scripts 108 represent software code or applications (e.g., compiled software code) that directs operation of processors, as described herein. As described herein, different scripts 108 can direct the processors to perform different operations on or with the data. For example, the scripts 108 can represent software code written in SQL that directs how the data storage system 104 handles and/or examines data stored in the implementation data store 106. The scripts 108 can be stored in a centralized location (e.g., within the data storage system 104) so that the scripts 108 can be easily accessible to apply to any or all the data from different production data sources 110.

While only three scripts 108, a single data storage system 104, and a single implementation data store 106 are shown in FIG. 1, optionally, fewer or more than three scripts 108 can be provided, more than a single data storage system 104 can be provided, and more than one implementation data store 106 can be used.

The implementation data store 106 receives and stores data from one or more production data sources 110 (e.g., data sources 110A-C, shown as "Production Data Source #1," "Production Data Source #2," and "Production Data Source #n" in FIG. 1). While three data sources 110 are shown, optionally, fewer or more data sources 110 may be used. The production data sources 110 can be computerized systems that provide the data being analyzed by the data validation system 100 for validation and used to track and/or generate action plans for entities. The production data sources 110 can be systems that are external to and not part of the data validation system 100. The production data sources 110 can represent databases or other computerized storage systems (e.g., tangible and non-transitory computer-readable media) that send different sets of data to the implementation data store 106 via one or more computerized communication networks 112. As some examples, the production data sources 110 can include databases located at medical offices, medical clinics, hospitals, pharmacies, laboratories, educational facilities or entities, financial institutions, manufacturing facilities, insurance companies, or the like. The networks 112 can represent one or more wired and/or wireless communication networks, such as the Internet, one or more intranets, one or more other wide area networks, and/or one or more local area networks that electronically communicate data.

The data that is received from the production data source(s) 110 can include a variety of different types or categories of data. The examples provided herein are not limiting on all embodiments of the inventive subject matter described herein. With respect to healthcare, the data can include demographic data, electronic medical record (EMR) encounter data, medical claim data, pharmacy claim data, lab result data, medical metric data, admit data, discharge data, or transfer data for at least one patient. The demographic data can identify the name, gender, age, address, or the like, of the patient. The EMR encounter data can include information on medical events involving the patient, such as medical tests run on the patient, the results of the medical tests, image data of the patient, or the like. The medical claim data can include information on medical claims submitted by and/or on behalf of the patient to a health benefit plan manager, such as information on health insurance claims. The pharmacy claim data can include information on pharmacy claims submitted by and/or on behalf of the patient to a pharmacy benefit plan manager, such as information on prescription fills and refills of medications. The lab result data can include information on results of laboratory tests, such as the results of blood tests. The medical metric data includes information representative of a state of health or disease of a person based on other medical data. For example, a body mass index, hemoglobin A1c test result, life expectancy, or the like, can be medical metrics. Admit data includes information on patients being admitted to a medical facility, such as a hospital or outpatient surgical center. Discharge data similarly includes information on patients being discharged from such a medical facility. Transfer data includes information on patients being transferred from one medical facility to another medical facility. Other types of data may be received and stored. For example, financial data such as bank accounts, financial investments, demographic data, or the like, can be obtained and used to generate an action plan. Other data can include educational data, such as data on classes currently being taken, classes required for a degree or certification, hours or classes completed, demographic data, or the like.

The action plan includes one or more operations or action to perform with respect to the person associated with the plan. With respect to healthcare data, an action plan can include medical treatment operations to perform on or with the person, medication to be prescribed to the person, laboratory tests to perform on the person, schedules of medical facility visits for the person, and the like. The healthcare data of that person that is obtained from the production data sources 110 can identify health risks or conditions of the person and can be used to determine what actions can be performed to help that person live a healthier life. For example, the healthcare data of a person may indicate that the person is a type I diabetic. The action plan derived from the healthcare data can recommend that the person visit an endocrinologist at least three times per year, that the person test their blood glucose level at least four times per day, that the person test their hemoglobin A1c at least three times per year, that the person undergo an eye examination at least once a year, and so on.

If the data used to create and/or track adherence to the action plan is not accurate, then the action plan may not be accurately tracked and/or created. For example, a production data source 110 may input incorrect data, leaves some data fields empty, places inaccurate default values in data fields, or the like. This can result in the action plan not indicating that a person has completed one or more actions (when the person has completed the action(s)), the action plan recommending an action that is inappropriate for the person (e.g., recommending annual mammography examinations for a male having no history of breast cancer), or other faults with the action plan. The data validation system 100 operates to receive, examine, and validate (or invalidate) different sets of data from the production data sources 110 for use in creating and/or tracking action plans. In one embodiment, the data validation system 100 does not create or track the action plans but validates data for use in creation and/or tracking of action plans. Instead, the production data sources 110 receive validation decisions on the data and then create and/or track action plans using the validated data. Alternatively, the data validation system 100 can create and/or track the action plans.

The data received from the production data sources 110 is stored in the implementation data store 106 by the data storage system 104. The data storage system 104 can store the data from one or several production data sources 110 without changing the data or by changing the format of at least some portions of the data. For example, the data can be directly received at the implementation data store 106 via the networks 112 and from the one or more production data sources 110 without modification of the data.

Alternatively, one or more portions of the data can be modified between the production data source 110 and the implementation data store 106. An intermediate server or computer 118 ("Intermediate Machine" in FIG. 1) can receive the data from one or more production data sources 110 prior to the data being received by the implementation data store 106. The intermediate computer 118 can modify one or more portions of the data within the intermediate computer 118 prior to sending the modified data to the implementation data store 106. For example, the intermediate computer 118 can normalize or otherwise conform the data to one or more requirements of the data storage system 104.

The data storage system 104 can apply an evaluation rule or several evaluation rules to one or more sets or groups of the data in the implementation data store 106. These evaluation rules can be applied to the data by running one or more of the previously created scripts 108. The scripts 108 can apply the evaluation rules by comparing the data with criteria, by examining contents or formats of the data, by comparing different portions of the data with each other, or the like.

The scripts 108 may be previously created in that one or more persons or artificial intelligence computer systems may have created the scripts 108 before the data was received by the implementation data store 106. The scripts 108 may have been written by higher level analysts, such as persons having at least a designated level or amount of education, training, and/or experience in writing scripts 108, such as a person who has achieved at least a designated number of years of education in software programming, a person who has completed at least a designated number of programming classes or course works, a person who has received one or more certifications related to writing code in the language used by the data storage system 104, a person who has written at least a designated number of scripts 108 to control operation of the data storage system 104, a person who has worked at one or more jobs writing scripts 108 to control operation of the data storage system 104, or the like. For example, the scripts 108 may be authored by person(s) trained and/or educated to write software code using SQL or another programming or database query language. Optionally, the scripts 108 can be written in a visual manner, such as by dragging and dropping icons indicative of different actions to take with the data into a coding window. This can allow for the scripts 108 to be written by analysts that may not necessarily have the coding experience or knowledge to type out the scripts 108, but that have the experience and knowledge to know what operations need to be performed by the scripts 108 to apply the evaluation rules to the data, as described herein.

The evaluation rules applied to the data by the scripts 108 output one or more deviation measures. A deviation measure can be output for each evaluation rule, for each of one or more sets of data (to which at least one evaluation rule is applied), or the like. The deviation measure can indicate whether the data has one or more exceptions from a designated expectation and optionally can indicate how much the data differs from the designated expectation. For example, the deviation measure can indicate how much the data varies from a baseline value, how much the data varies within the set, differences between data in different sets, differences between different portions of the data within the same set, or the like. In one embodiment, larger deviation measures indicate that the data varies more than for smaller deviation measures. Larger deviation measures can indicate problems with the data and can indicate to a lower level analyst that the data cannot be validated or that one or more issues with the data needs to be fixed or changed before validating the data for use in tracking and/or creating an action plan.

The deviation measure that is determined can be presented to one or more analysts for review. In one embodiment, at least one analyst is a person using a computerized user device 114 (e.g., user devices 114A-C) that are communicatively coupled with the data storage system 104 by one or more computerized communication networks 116. For example, the user devices 114 can each access and/or communicate with the controller 102 and the data storage system 104 via a web browser or other software applications running on the user device 114. The network(s) 116 can represent a different network(s) than the network(s) 112, at least one network that differs from the network(s) 112, or one or more of the same networks as the network(s) 112. For example, the network 116 may be a private or secure communication network. The deviation measure(s) can be presented on an output device of the user device 114, such as an electronic display, a printed paper, a speaker, or the like.

In one embodiment, the evaluation rules are applied to the data and the deviation measure is presented to the analyst without revealing protected information in the data to the analyst. For example, some portions of the data can include private or confidential information, such as protected health information (as defined by the Health Insurance Portability and Accountability Act as of the filing of this patent application), confidential financial information, confidential educational information, or the like. The lower level analyst may not be legally or contractually permitted to view the protected information. Optionally, the controller 102 can apply the evaluation rules and present the deviation measure with the protected information not being presented with the deviation measure, with the protected information blacked out or otherwise obscured from view (e.g., made to appear blurry or otherwise illegible), or the like.

Additionally or alternatively, one or more of the analysts that review deviation measures may be automated computerized devices. For example, an analyst can be represented by a user device 114 can be an artificial intelligence software application operating via one or more processors under the direction of software applications. The artificial intelligence analyst can operate using a computerized neural network that automatically examines the deviation measures to determine whether to validate the data associated with the deviation measure.

The evaluation rules can be automatically applied to one or more sets of the data. For example, certain evaluation rules can be automatically applied by the controller 102 at times based on a designated schedule. Optionally, the evaluation rules can be applied responsive to data-loading events occurring. For example, the controller 102 can automatically apply one or more evaluation rules to the data when at least a designated amount of data is received from a production data source 110, when data of a designated type or category of data (e.g., demographic data, laboratory data, financial account data, etc.) is received, or based on another triggering event related to the loading of data into the implementation data store 106 from the one or more production data sources 110. Optionally, one or more of the evaluation rules can be applied on an ad hoc basis.

In one embodiment, one or more of the scripts 108 can be re-used for multiple different sets of data. For example, the evaluation rules that are run by the scripts 108 can be re-used for different sets of data originating from different production data sources 110. This can prevent the same or substantially similar scripts 108 being written for the data coming from each different production data source 110. As one example, a script 108 that examines the number of health insurance claims submitted each month by members of a health insurance plan (to identify large changes in the monthly number of claims) can be written once for the data from the production data source 110A by a higher level analyst or coder. This same script 108 can then be re-used to count insurance claims in the data from the production data source 110B and/or 110C.

A restricted list of defined validation decisions for the set(s) of data associated with the deviation measure can be presented to the analyst for selection. This list can include prescribed remediations to take in response to examining the deviation measure. The list may be restricted to limit which prescribed remediations are taken. The lower level analyst may be prevented from taking certain prescribed remediations based on the lesser training and/or education of the analyst relative to the person(s) who created the scripts 108 used to generate the deviation measure. The author(s) of the scripts 108 may be trained to write code in the language of the data storage system 104 while the analyst may not be trained to write code in this language. For example, the scripts 108 may be written using SQL, but the analyst may not be trained or certified to write code using SQL.

The deviation measure may indicate problems with the associated data that require writing code to access and/or modify the data in the implementation data store 106 via the data storage system 104. But, the analyst may not be trained to write this code and thus either unable to do so or unable to do so with a high degree of accuracy. To prevent such an analyst from writing incorrect code or modifying the data in the implementation data store 106 in an undesirable manner, the analyst may only be allowed to implement the actions in the restricted list.

As one example, the restricted list can include a validation action. This action optionally can be referred to as a pass decision. Selecting the validation action (e.g., using an input device of the user device 114, such as a touchscreen, electronic mouse, keyboard, stylus, or the like) directs the user device 114 to send a signal to the controller 102 indicating that the data is approved for use in tracking and/or generating an action plan. Stated differently, the data is approved for use in the action plan.

As another example, the restricted list can include an investigation action. This action optionally can be referred to as a pending action. Selecting the investigation action directs the user device 114 to send a signal to the controller 102 that directs the controller 102 to mark or flag the data for further investigation or analysis. For example, the controller 102 may append information to the data indicating that the data needs to be examined by another analyst. This other analyst may be more highly trained than the analyst that selected the investigation action. For example, this other analyst may be trained to write scripts 108 in the language of the data storage system 104 to more closely examine and/or modify the contents of the data. The data that is marked or flagged by the controller 102 may be used in tracking or creating the action plan before and/or while the other analyst performs the additional investigation of the data. Alternatively, the data that is marked or flagged by the controller 102 may be quarantined and not used in tracking or creating the action plan before and/or while the other analyst performs the additional investigation of the data.

As another example, the restricted list can include a rejection action. This action optionally can be referred to as a fail decision. Selecting the rejection action directs the user device 114 to send a signal to the controller 102 that directs the controller 102 to not use the data in tracking and/or generating an action plan. Stated differently, the data is not approved for use in the action plan. Selection of this decision indicates that the data included one or more unacceptable exceptions to the designated expectation(s) represented by the evaluation rule(s).

Responsive to receiving a fail decision or rejection action, the user device 114 and/or controller 102 can build an inspection data set for a higher-level analyst or reviewer to examine to further investigate why the evaluation rule provided the deviation measure. This inspection data set can include the data to which the evaluation rule was applied or an identifier of the data. The higher-level analyst can then examine the identified data to determine how or why the data is providing the deviation measure when the evaluation rule is applied. This can help correct errors in the data and/or to modify the evaluation rule so that correct data is not misidentified as erroneous data.

Optionally, the controller 102 can direct the data storage system 104 to take one or more data loading actions responsive to the analyst providing the rejection action or fail decision. These loading actions can include the data storage system 104 stopping the receipt (also referred to as loading) of data from one or more production data sources 110. For example, the data storage system 104 can stop additional data from being received (and/or stored) from the production data source 110 that provided the data associated with the fail or rejection decision. Stopping the loading of additional data from this source 110 can allow for the data storage system 104 from storing more potentially incorrect data from the source 110 while data from other sources 110 continues to be received and stored in the implementation data store 106. The owner or operator of the production data source 110 can then be educated or instructed on how to change how the data is entered, formatted, or the like, so that future data from the production data source 110 does not result in the same fail or rejection decision for the same reason.

The restricted list of defined validation decisions can include an indeterminate decision. Selection of the indeterminate decision indicates that the analyst is unable to determine whether the deviation measure did or did not conform to the limit described above. For example, some deviation measures require a subjective analysis of whether the data appears to be acceptable. Some deviation measures clearly indicate that the data is or is not acceptable, but some deviation measures may not so clearly define acceptable or unacceptable data. The analyst can select the intermediate decision in situations where the deviation measure does not clearly indicate that the data is acceptable, but also does not indicate that the data is unacceptable. Responsive to selection of the intermediate decision, the deviation measure can be provided to a higher-level analyst for further investigation to determine whether the data is validated, similar to the investigation action.

Responsive to receiving one or more of the fail decision or the indeterminate decision from the user device 114, the user device 114 and/or controller 102 can receive additional identifying data from the analyst. This information can be appended to the one or more sets of the data associated with the decision based on input provided by the analyst. The identifying data can represent the evaluation rule(s) applied to the data to result in the decision and/or a proposed solution operation. The proposed operation solution can be a suggestion made by the analyst on how to modify the set(s) of data to avoid the fail decision. For example, the analyst may recognize that modifying one or more fields in the data and re-applying the evaluation rule(s) to the data may result in a different deviation measure that would not receive the fail or indeterminate decision. This suggested modification can be provided to the controller 102 so that the controller 102 can communicate the modification to a higher-level analyst for review and potential implementation.

Optionally, the suggested modification may be provided by the analyst for application for additional, future, or upcoming data (e.g., data that is not yet received from the production data store(s) 110). For example, the analysts may determine that a production data source 110 is incorrectly entering one or more fields of the data, is arranging the data in an incorrect format, or the like. The suggested modification can be communicated to a higher-level analyst, a person in contact with the entity or customer associated with the production data source 110 (that provides the data needing the modification), or the like. This suggested modification can be used to educate the owner or operator of the production data source 110 to ensure that future data from the production data source 110 does not suffer from the same problems that were discovered by the analyst examining the deviation measure and providing the suggested modification.

Figure 2:
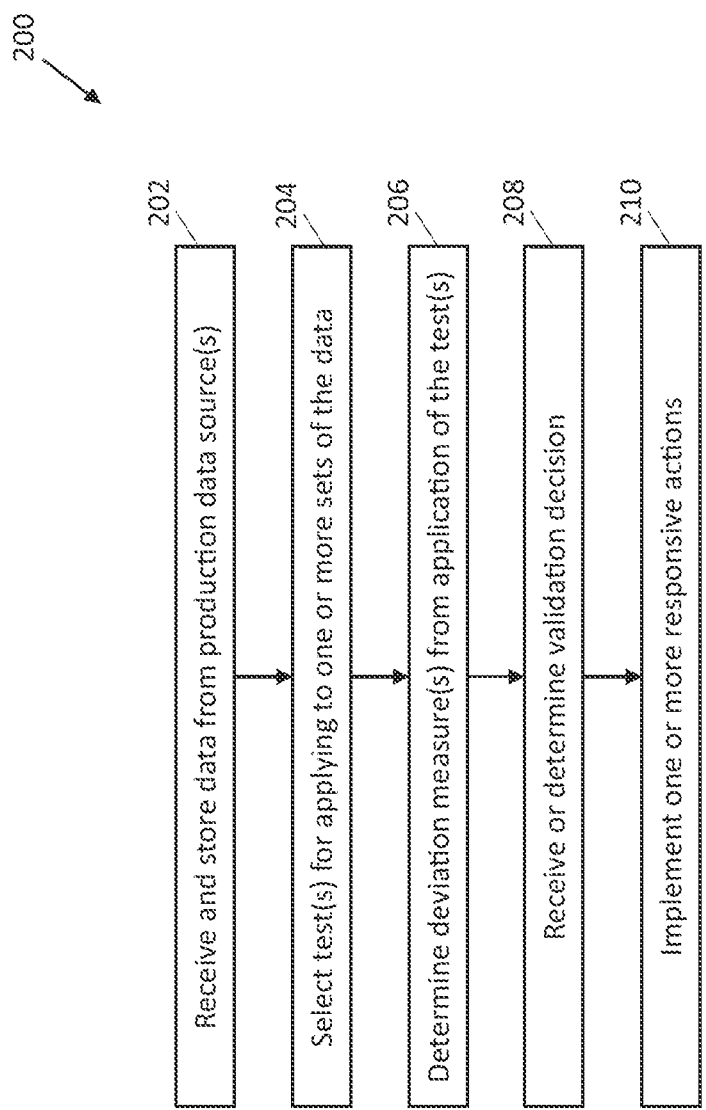
FIG. 2 illustrates a flowchart of one embodiment of a method for validating data.

FIG. 2 illustrates a flowchart of one embodiment of a method 200 for validating data. The method 200 describes operations that can be performed by the data validation system 100 in connection with examining data for use in creating and/or tracking completion of action plans. At 202, data is received and stored at an implementation data store from one or more production data sources. The data can be received via one or more communication networks. Optionally, the data is received from the production data sources without modifying the data. Alternatively, the data may be modified to change a format, syntax, or the like, but not the information represented by the data, prior to storing the data at the implementation data store.

At 204, one or more evaluation rules are selected for applying to some or all the data. The evaluation rules can be selected by the controller of the data validation system described above. The controller can select the evaluation rules to be applied based on a schedule of when various evaluation rules are to be applied. The schedule can vary for different types or categories of the data, for different sets of data provided by different production data stores, or the like. The schedule can cause the evaluation rules to be automatically applied to the data. Optionally, a lower level analyst can select the evaluation rules to be applied to the data.

Figure 3:
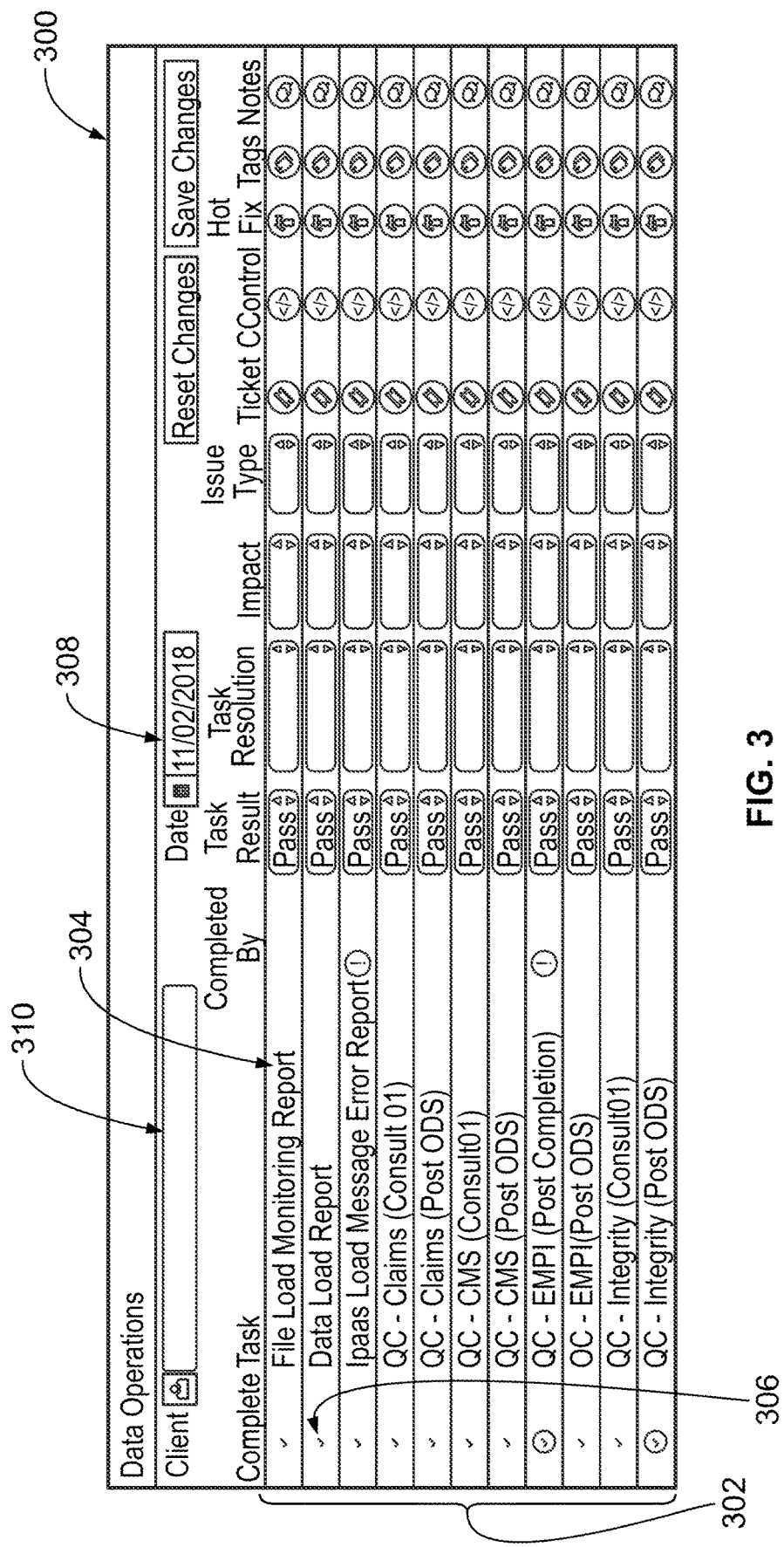
FIG. 3 illustrates part of a graphical user interface (GUI) that can be shown on one or more user devices shown in FIG. 1.

With continued reference to the flowchart of the method 200 shown in FIG. 2, FIG. 3 illustrates part of a graphical user interface (GUI) 300 that can be shown on one or more of the user devices 114 shown in FIG. 1. The GUI 300 provides a list, table, or other data structure 302 with various names of evaluation rules 304 in one column of the table 302. This table 302 provides the lower level analyst with a list of which evaluation rules 304 were performed or not performed (e.g., by displaying a completion indicator 306, such as a checkmark, to indicate that the evaluation rule 304 was completed). This can help the analyst to determine whether any additional evaluation rules need to be selected for application to the data.

The GUI 300 can provide the analyst with a date selector input area 308. The input area 308 is shown as a bar configured to receive a numeric or an alphanumeric text string (e.g., a date entered by the analyst). Alternatively, the input area 308 can be shown in another manner that allows an analyst to input a date. The controller 102 uses the date entered by the analyst in the input area 308 to obtain the results of the evaluation rules 304 ran on that date. For example, the list of evaluation rules 304 that are run each day and the associated results of the evaluation rules 304 (e.g., the completion icons 306, a null result icon 402 described below, the deviation measures, etc.) can be stored by the data storage system 104. The controller 102 (or data storage system 104) can retrieve the evaluation rules 304 that were run on a selected data and the results of those evaluation rules 304 based on the date input into the input area 308.

Optionally, the GUI 300 can provide the analyst with a source input area 310. The input area 310 is shown as a bar configured to receive a numeric or an alphanumeric text string (e.g., an entity name or identifier entered by the analyst). Alternatively, the input area 310 can be shown in another manner that allows an analyst to input information that identifies an entity, such as an owner or operator of a production data source 110. The controller 102 uses the identifying information entered by the analyst in the input area 310 to obtain the evaluation rules 304 and optionally the associated results of the evaluation rules 304 that are to be run on the data from the production data source 110 identified by the analyst. For example, different groups of evaluation rules 304 that are run each day and the associated results of the evaluation rules 304 (e.g., the completion icons 306, a null result icon 402 described below, the deviation measures, etc.) may be associated with different production data sources 110. The controller 102 (or data storage system 104) can retrieve the evaluation rules 304 that were or are to be run for a production data source 110 identified in the input area 310.

At 206, one or more deviation measures are determined from application of the evaluation rule(s) to the data. As described above, a deviation measure can indicate how much the data varies from a baseline value, how much the data varies within the set, differences between data in different sets, differences between different portions of the data within the same set, or the like. With continued reference to the flowchart of the method 200 shown in FIG. 2, FIG. 4 illustrates part of another GUI 400 displaying deviation measures on one or more of the user devices 114 shown in FIG. 1. The controller 102 can direct the user device 114 to display a null result icon 402 next to one or more of the evaluation rules 304. This null result icon 402 is shown as a circle around the completion indicator 306, but optionally can be shown in another way. The null result icon 402 indicates that an evaluation rule was run on a data set, but that no results were returned as output of the evaluation rule. For example, an evaluation rule could be run on a data set to output a count of the number of medical records in the data set that are associated with persons of a selected gender (e.g., all female medical records). If there are no medical records associated with females, then the output of the evaluation rule may be zero or null. The controller 102 can direct the null result icon 402 to be displayed next to this evaluation rule on the user device 114.

FIG. 5 illustrates part of another GUI 500 that displays deviation measures 502 on one or more of the user devices 114 shown in FIG. 1. In the illustrated example, an evaluation rule is applied to demographic data to identify how many persons associated with the data are male 504, female 506, or unknown from the contents of the data. The number of gender unknowns indicates that the data may not be formatted correctly or may include incorrect data entries (e.g., entries that are not associated with any gender). The number of gender unknowns can be the deviation measure 502 for the evaluation rule as the evaluation rule may seek to identify all entries in the data as male 504 or female 506. In the illustrated embodiment, the deviation measure 502 is zero for all ages in the data, as all entries in the data are associated by the evaluation rule as male 504 or female 506.

Figure 6:
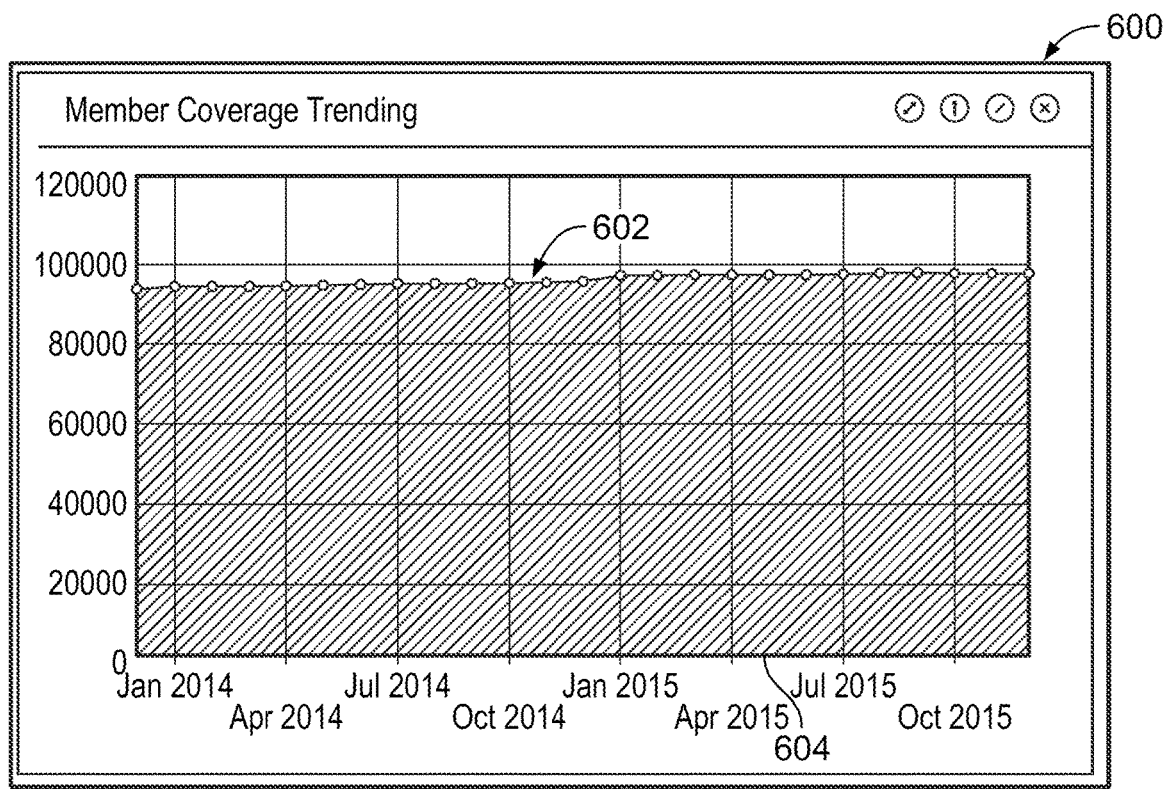
FIG. 6 illustrates part of another GUI that displays deviation measures on one or more of the user devices shown in FIG. 1.

FIG. 6 illustrates part of another GUI 600 that displays deviation measures 602 on one or more of the user devices 114 shown in FIG. 1. In the illustrated example, an evaluation rule is applied to demographic data to identify how many persons are identified in the data as members of a benefit plan, such as a medical insurance plan. The deviation measure 602 is represented as the number of members in the benefit plan at different times along a horizontal axis 604.

Optionally, the deviation measure 602 can be a slope of a line or curve connecting the different measures of members of the benefit plan over the different months. This slope can be compared to a designated threshold or range of slopes to determine whether the slope indicates that the rate of change of membership in the benefit plan is expected or if the rate of change in membership is decreasing or increasing faster than expected. A slope that indicates a rate of change that is larger than expected can indicate that the data cannot be validated while a slope indicating an acceptable or expected rate of change can indicate that the data can be validated.

Figure 7:
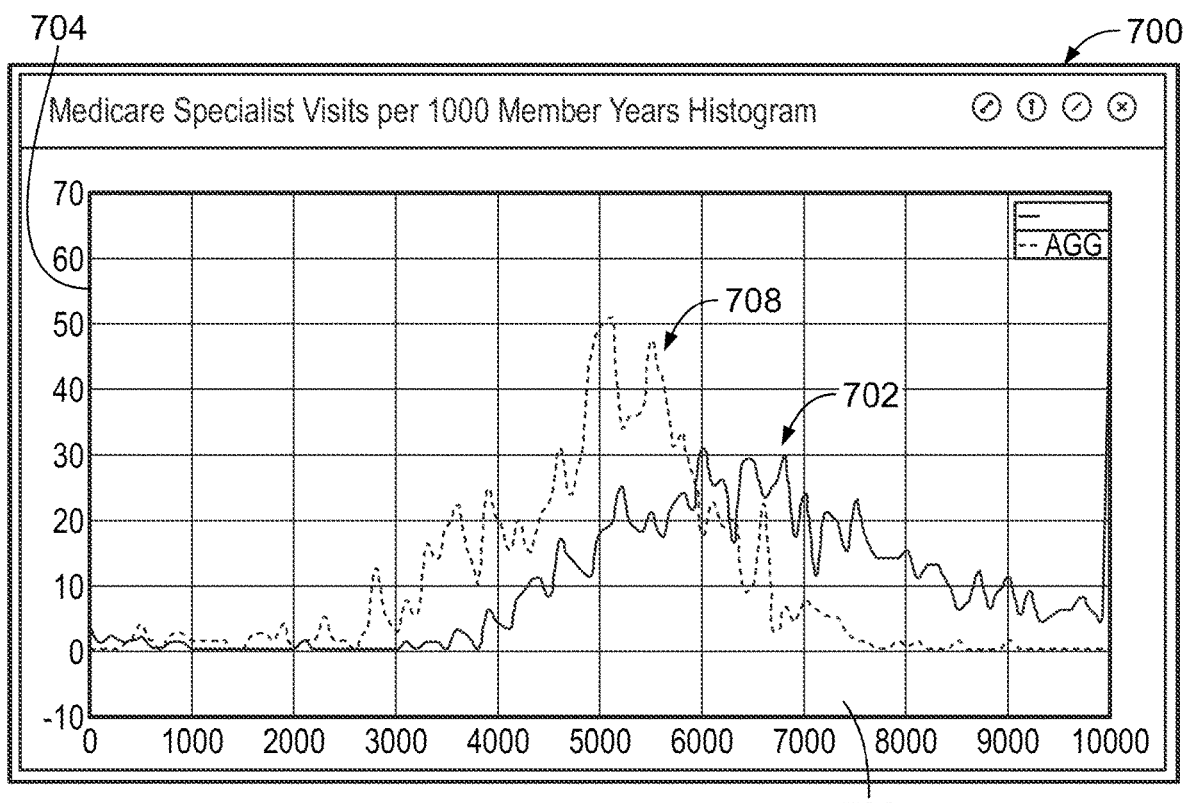
FIG. 7 illustrates part of another GUI that displays a deviation measure on one or more of the user devices shown in FIG. 1.

FIG. 7 illustrates part of another GUI 700 that displays a deviation measure on one or more of the user devices 114 shown in FIG. 1. In the illustrated example, an evaluation rule is applied to one set of data to determine a relationship 702 between visits to a medical specialist by members of the Medicare health insurance plan (along a vertical axis 704) per one thousand-member years (along a horizontal axis 706). The evaluation rule is also applied to determine a baseline relationship 708 between visits to a medical specialist by members of the Medicare health insurance plan per one thousand-member years. The relationship 702 is calculated from the set(s) of data being evaluated, while the baseline relationship 708 is calculated from an aggregate set of multiple additional sets of data, such as all data in the implementation data store containing information on visits to medical specialists by members of the Medicare health insurance plan. The deviation measure can be the difference between the relationships 702, 708. This type of deviation measure is a partially subjective deviation measure because the deviation measure relies on how the lower level analyst views the differences between the relationships 702, 708.

The relationships 702, 708 can be visually examined by a lower level analyst to determine whether the relationships 702, 708 are similar or the same, whether the relationships 702, 708 are starkly different, or whether the relationships 702, 708 are somewhere between being similar or starkly different. If the relationships 702, 708 have more similarities than dissimilarities (e.g., largest peaks are within a designated range of each other, such as 5%; widths of the portions of the relationships 702, 708 that rise above the horizontal axis 706 are within the designated range of each other; locations of peaks of the relationships 702, 708 are within the designated range of each other along the horizontal axis 706; etc.), then the relationships 702, 708 may indicate a pass or acceptable deviation measure. This can indicate that the data from which the relationship 702 is derived is validated. If the relationships 702, 708 have more dissimilarities than similarities, then the relationships 702, 708 may indicate a fail deviation measure. This can indicate that the data from which the relationship 702 is derived is not validated. If the relationships 702, 708 cannot be determined to be similar or dissimilar, then the analyst or controller 102 can indicate that the relationship 702 does not pass or fail the evaluation rule 304, and that additional examination by a higher-level analyst and/or another evaluation rule 304 is needed before validating the data from which the relationship 702 is derived.

In the illustrated example, the relationship 702, 708 may be found to be more similar than dissimilar (and therefore obtain a validation decision on the data) except for a significant increase 710 in the relationship along the far-right side of the horizontal axis 706. This significant increase 710 does not have another increase on the right side of the relationship 708. Therefore, the presence of the increase 710 in the relationship 702 but not the relationship 708 indicates that the data cannot be validated (e.g., indicates a large deviation measure).

Figure 8:
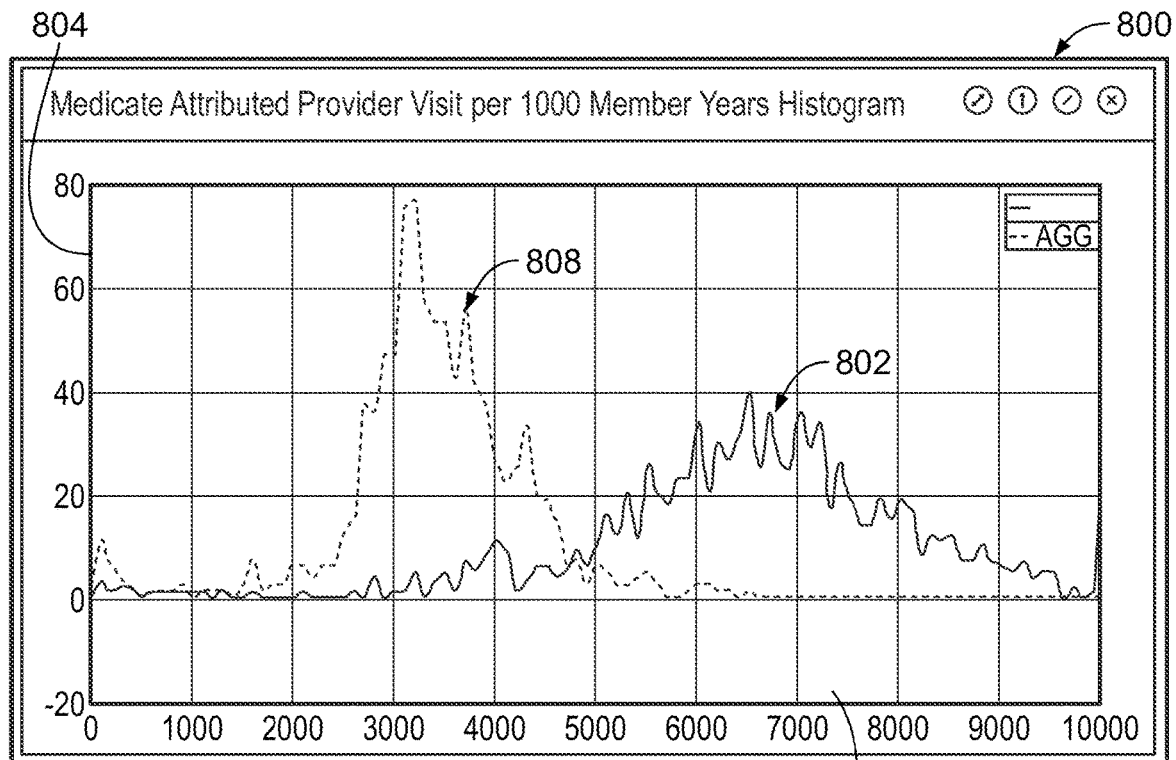
FIG. 8 illustrates part of another GUI that displays a deviation measure on one or more of the user devices shown in FIG. 1.

FIG. 8 illustrates part of another GUI 800 that displays a deviation measure on one or more of the user devices 114 shown in FIG. 1. In the illustrated example, an evaluation rule is applied to one set of data to determine a relationship 802 between visits to a Medicare-attributed provider by members of the Medicare health insurance plan (along a vertical axis 704) per one thousand-member years (along the horizontal axis 706). The evaluation rule is also applied to determine a baseline relationship 808 between visits to a Medicare-attributed provider by members of the Medicare health insurance plan per one thousand-member years. The relationship 802 is calculated from the set(s) of data being evaluated, while the baseline relationship 808 is calculated from an aggregate set of multiple additional sets of data, such as all data in the implementation data store containing information on visits to medical specialists by members of the Medicare health insurance plan. The deviation measure can be the difference between the relationships 802, 808. This type of deviation measure also is a partially subjective deviation measure because the deviation measure relies on how the lower level analyst views the differences between the relationships 802, 808.

FIG. 11 illustrates another GUI 1100 that displays a deviation measure on one or more of the user devices 114 shown in FIG. 1. In the illustrated example, an evaluation rule is applied to one set of data to determine an average error count 1102 among the data. This error count 1102 can indicate the average number of loading errors that occurred while trying to save medical records from one or more production data sources 110 to the implementation data store 106. For example, if a file was corrupted or otherwise unable to be saved in its entirety in the implementation data store 106, then this could indicate one error. The lower level analyst can compare the average error counts 1102 with a threshold error count 1104 to determine whether to validate the data. The threshold error count 1104 can be one or more designated standard deviations of errors in the loading of data. In the illustrated example, all the average error counts 1102 are smaller than the corresponding threshold error counts 1104. As a result, the lower level analyst can validate the data.

As shown in the examples of the GUIs 400, 500, 600, 700, 800, 1100 of FIGS. 4 through 8 and FIG. 10, no protected information is visible to the analyst examining the deviation measures. Instead, anonymized results or charts are displayed. Optionally, protected information may be covered or otherwise obscured from view.

Returning to the description of the flowchart of the method 200 shown in FIG. 2, at 208, a validation decision is received or made based on the deviation measure. The deviation measure can be presented on an output device of a user device 114 to allow the lower level analyst to examine the deviation measure and select a validation decision. Optionally, the analyst can be an artificial intelligence program that automatically examines the deviation measure and selects the validation decision.

Figure 9:
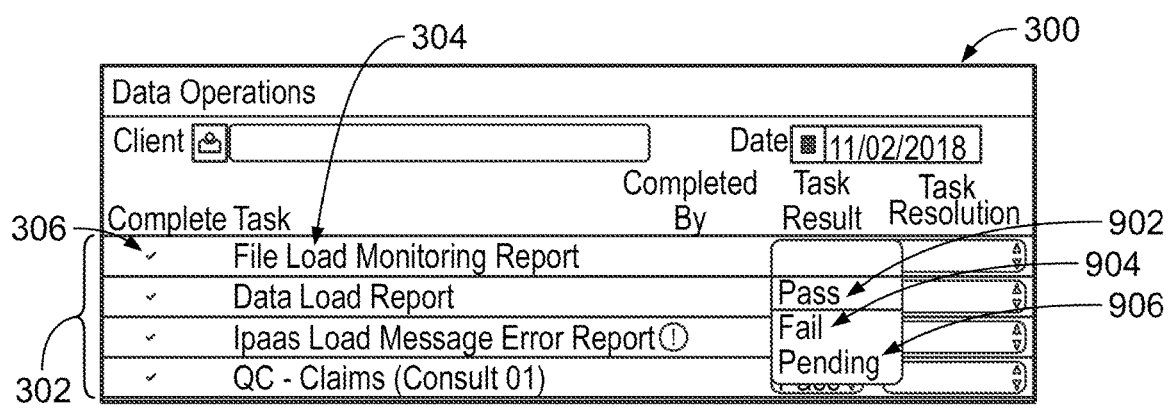
FIG. 9 illustrates another view of the GUI shown in FIG. 3 according to one example.

FIG. 9 illustrates another view of the GUI 300 shown in FIG. 3 according to one example. The GUI 300 can provide a drop-down menu 900 or other interface to allow the analyst to select the validation decision. In the illustrated example, this menu 900 provides the restricted list of defined validation decisions for the evaluation rule results. The analyst can use the menu 900 to select a pass decision or validation action 902 ("Pass" in FIG. 9), a rejection action or fail decision 904 ("Fail" in FIG. 9), or an investigation action or indeterminate decision 906 ("Pending" in FIG. 9).

With respect to the deviation measure shown in the GUI 400 of FIG. 4, the controller 102 can automatically determine a rejection action or fail decision 904 as the validation decision. Optionally, the analyst can make this validation decision based on the deviation measure. The evaluation rule was performed on a data set, and no records were found in the data set that satisfied the evaluation rule. The deviation measure for this evaluation rule can be the number of records found in the data that satisfy the evaluation rule. Because no matching records were found, the controller 102 can automatically (e.g., without analyst or other operator intervention) determine that the data failed the evaluation rule and is rejected (e.g., a rejection action or fail decision 904).

With respect to the deviation measure shown in the GUI 500 of FIG. 5, the controller 102 can automatically determine a validation action or pass decision 902 as the validation decision. Optionally, the analyst can make this validation decision based on the deviation measure. The results of the evaluation rule indicate that all records in the data set have an identified gender and that no records have incorrect data or are missing data that allows automated identification of a gender.

With respect to the deviation measure shown in the GUI 600 of FIG. 6, the controller 102 can automatically determine a validation action or pass decision 902 as the validation decision. Optionally, the analyst can make this validation decision based on the deviation measure. The results of the evaluation rule indicate that the number of covered members is not significantly changing over time. A significant change in the number of covered members (e.g., a change that is larger than a threshold, such as larger than a 5% change) can indicate that the data failed the evaluation rule or requires more investigation. But, because the number of covered members does not significantly change, the data represented in FIG. 6 passes the evaluation rule (and may be validated).

With respect to the deviation measure shown in the GUIs 700, 800 of FIGS. 7 and 8, the analyst can determine whether the evaluation rule relationships 702, 802 have a similar shape, size (e.g., along the vertical axis 704), and/or location (e.g., along the horizontal axis 706) as the baseline or aggregate relationship 708, 808. In the GUI 700, although the relationships 702, 708 do have different shapes or sizes, the relationships 702, 708 may be identified by the analyst as being more similar than dissimilar. As a result, the analyst may make a validation action or pass decision 902 as the validation decision. But, in the GUI 800, the relationships 802, 808 have more significantly different shapes, sizes, and locations. As a result, the analyst may make a rejection action or fail decision 906 as the validation decision. Optionally, the analyst may be unable to validate, pass, fail, or reject the evaluation rule results shown in FIGS. 7 and 8. The analyst can select the investigation action or indeterminate decision 906 as a result.

Returning to the description of the flowchart of the method 200 shown in FIG. 2, at 210, one or more responsive actions are implemented. The responsive action that is implemented can be based on the validation decision selected at 208.

Figure 10:
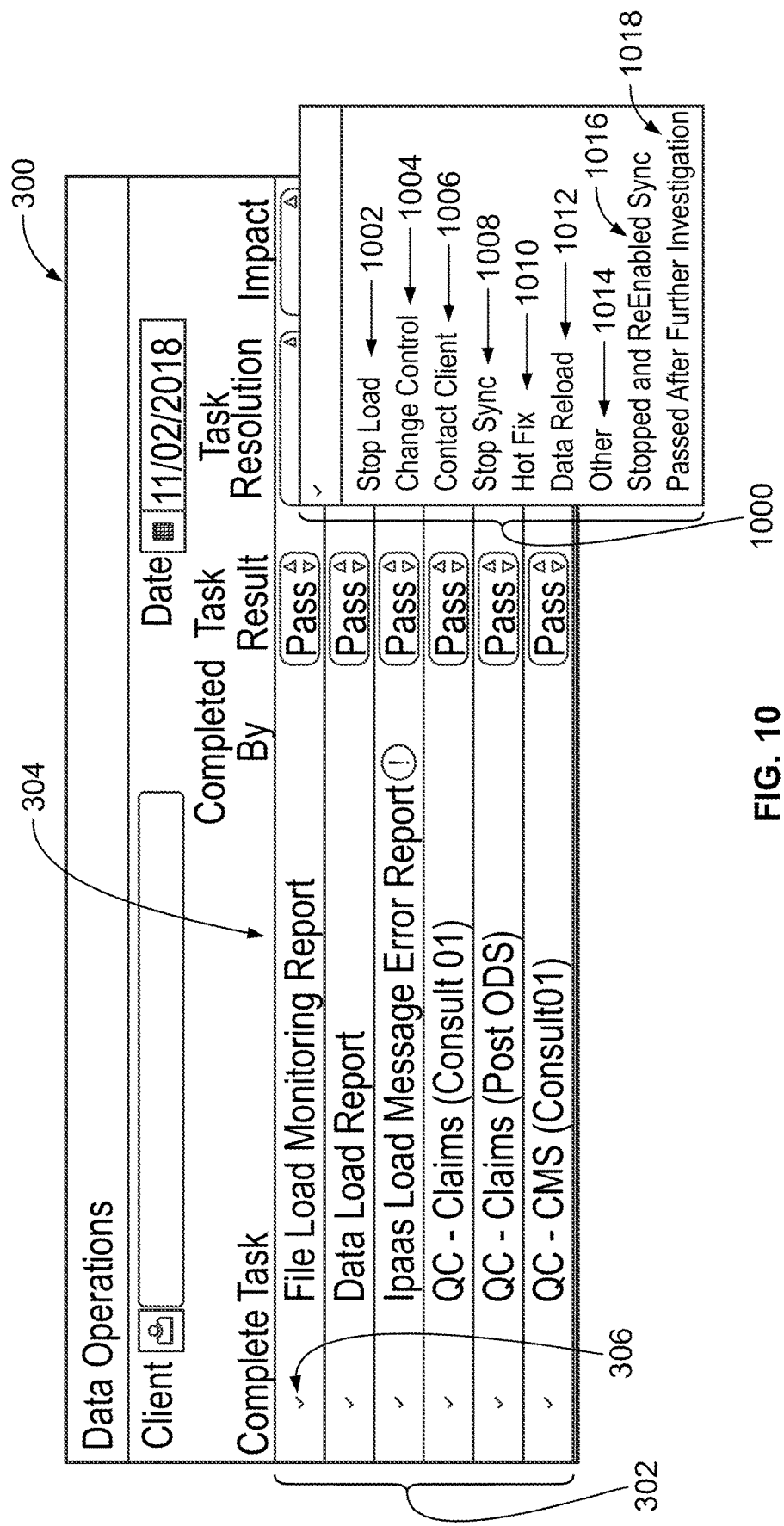
FIG. 10 illustrates another portion of the GUI of FIG. 3 that can be used to implement one or more responsive actions.

FIG. 10 illustrates another portion of the GUI 300 of FIG. 3 that can be used to implement one or more prescribed remediations to validation decisions. In the illustrated embodiment, the controller 102 or user device 114 provides the analyst with a menu 1000 of several responsive actions to implement as prescribed remediations to validation decisions. In the illustrated example, the analyst can select a stop load action 1002 to stop the loading of data from the same production data source(s) 110 that provided the data on which the validation decision was made. Optionally, this stop load action 1002 can prevent additional data from being saved into the implementation data store 106 from the production data source 110.

A change control action 1004 can be selected to change the data or change configuration of an evaluation rule. Selection of this action 1004 can allow the lower level analyst (or may only allow a higher-level analyst) to change the data and/or the evaluation rule such that re-applying the rule to the data after the change results in an acceptable deviation measure (which then results in a validation decision).

A contact client action 1006 can be selected to direct the controller 102 to automatically send a message to the production data source 110 that is the origin of the data giving rise to selection of the action 1006. This message can notify the production data source 110 (or the owner or operator of the production data source 110) of the deviation measure and/or that the data from the production data source 110 appears to be erroneous. Optionally, the message can direct or request that the production data source 110 modify the data and/or future data to reduce the number of additional deviation measures associated with the data from that production data source 110.

A stop sync action 1008 can be selected to direct the data storage system 104 to stop or pause the syncing of data back to the production data source(s) 110 from the implementation data store 106. As described above, the data is loaded into the implementation data store 106 from a production data source 110, examined for validation, and then provided back to the production data source 110 (at least the portion of the data that has been validated). This providing of the validated data back to the production data source 110 is the syncing of the data. An analyst can select the stop sync action 1008 to at least temporarily pause the syncing of data back to the production data source 110.

A hot fix action 1010 can be selected to indicate that the lower level analyst discovered a problem with the production data source 110 that supplied the data on which the evaluation rule was applied. Optionally, this action 1010 can be selected to request that a script 108 be modified. Selecting the hot fix action 1010 can cause a signal to be sent to the production data source 110 or a higher-level analyst so that the production data source 110 can fix the problem and/or the higher level analyst can work with the owner or operator of the production data source 110 to correct the problem and/or modify a script 108.

A data reload action 1012 can be selected to cause the evaluation rule giving rise to selection of the data reload action 1012 to be applied again, but to an updated set of the data. For example, the evaluation rule may be applied on a set of data that may be incomplete because the data is being loaded into the implementation data store 106 while the evaluation rule is applied. As another example, one or more errors during the loading of the data from the implementation data store 106 by the data storage system 104 to run the evaluation rule may have occurred. These factors may cause the deviation measure to be larger than expected. The data reload action 1012 can cause the controller 102 to send a message to a higher-level analyst to reload the data. Alternatively, the data reload action 1012 can cause the data storage system 104 to automatically obtain the set of data from the production data source 110 again and re-run the evaluation rule against this data set. This can allow the analyst to see if the deviation measure decreases or otherwise changes, thereby indicating an error in the loading of data from the implementation data store 106 by the data storage system 104 (and not an error in the data stored in the implementation data store 106).

The menu 1000 can include an "other" action 1014, which indicates that the analyst performed one or more other responsive actions not identified elsewhere in the menu 1000. The analyst can provide additional notes (described below) to further describe what other action 1014 was implemented.

A re-enable sync action 1016 can be selected to direct the controller 102 to send a message to a higher-level analyst. This message can request that the higher-level analyst data storage system stop or pause the use of data in the production data store 106 from the tracking and/or creation of action plans and then re-start the use of this data in the tracking and/or creation of action plans. For example, the analyst can select the re-enable sync action 1016 when a previous pause to the use of the data is terminated and the data can again be used. Alternatively, selection of the re-enable sync action 1016 can automatically initiate this re-start of use of the data.

A passed action 1018 can be selected to direct the data storage system 104 to treat the data as validated data (and use the data in tracking and/or creating action plans). This action 1018 can be selected responsive to the analyst previously rejecting or failing the data, investigating the cause of the deviation measure (giving rise to the previous rejection or failure), and then determining that the data can be used in the action plans. This can occur when the deviation measure may not accurately reflect whether the data is correct or includes errors.

One embodiment of the inventive subject matter described herein provides a method for validating data for use in one or more of tracking or generating an action plan. The method includes receiving the data at an implementation data store from one or more production data sources via one or more computerized communication networks, storing the data in the implementation data store using a data storage system, and applying evaluation rules to one or more sets of the data in the implementation data store. The evaluation rules are applied to the one or more sets of the data by running previously created scripts of commands of the data storage system. Applying the evaluation rules to the one or more sets of the data outputs a deviation measure for at least one of the sets of the data. The method also includes presenting, to an analyst, the deviation measure and a restricted list of defined validation decisions for the one or more sets of the data, receiving a selected validation decision in the restricted list from the analyst, and one or more of validating the one or more sets of the data for use in the action plan, rejecting the one or more sets of the data for use in the action plan, and/or identifying the one or more sets of the data as requiring additional analysis before validating the one or more sets of the data for use in the action plan.

Optionally, the data storage system is one or more of a relational data storage system, a document storage system, or an object database system.

Optionally, the analyst is a human being.

Optionally, the analyst is an artificial intelligence computerized system.

Optionally, the selected validation decision is received from the analyst having one or more of a training level or an experience level below a designated level associated with writing the previously created scripts of the commands.

Optionally, the data includes one or more of demographic data, electronic medical record (EMR) encounter data, medical claim data, pharmacy claim data, lab result data, medical metric data, admit data, discharge data, or transfer data for at least one patient.

Optionally, the one or more production data sources include one or more databases at one or more medical offices, medical clinics, pharmacies, laboratories, educational entities, or financial institutions.

Optionally, the data is directly received at the implementation data store from the one or more production data sources without modification of the data.

Optionally, the method also includes receiving the data at an intermediate computer server from the one or more production data sources and prior to sending the data to the implementation data store and modifying one or more portions of the data within the intermediate computer server to one or more of normalize or conform the data to one or more requirements of the data storage system.

Optionally, the evaluation rules are applied to the one or more sets of the data and the deviation measure is presented to the analyst without revealing protected information in the data to the analyst.

Optionally, applying the evaluation rules to the one or more sets of the data automatically occurs based on a designated schedule.

Optionally, the method also includes determining when one or more data-loading events occur as the data is received at the implementation data store. Applying the evaluation rules to the one or more sets of the data can automatically occur based on occurrence of at least one of the data-loading events.

Optionally, the restricted list of defined validation decisions includes a pass decision indicating that the deviation measure of the one or more sets of the data conformed to a limit, a fail decision indicating that the deviation measure did not conform to the limit, or an indeterminate decision indicating that the analyst was unable to determine whether the deviation measure conformed or did not conform to the limit.

Optionally, the method also includes receiving identifying data to be appended to the one or more sets of the data based on input provided by the analyst responsive to receiving one or more of the fail decision or the indeterminate decision. The identifying data can represent one or more of the evaluation rules applied to the one or more sets of the data and/or a proposed solution operation to be used to modify the one or more sets of the data or upcoming data to avoid the fail decision on the one or more sets of the data or the upcoming data.

Optionally, the method also can include associating evaluation rule data with the one or more sets of the data responsive to rejecting the one or more sets of the data and communicating an identifier of the one or more sets of the data to a higher-level reviewer responsive to rejecting the one or more sets of the data. The higher-level reviewer can have one or more of a training level or an experience level above the designated level associated with writing the previously created scripts.

Optionally, the method also includes stopping loading of one or more additional sets of the data from a first production data source of the one or more production data sources responsive to rejecting the one or more sets of the data. The first production data source is associated with the one or more sets of the data that were rejected.

Optionally, the one or more sets of the data are used in the action plan to determine one or more additional medical treatment operations to perform in connection with at least one patient responsive to validating the one or more sets of the data for use in the action plan.

In one embodiment, a data validation system that validates data for use in one or more of tracking or generating an action plan for at least one person is provided. The data validation system includes an implementation data store configured to receive the data from one or more production data sources via one or more computerized communication networks, and one or more processors configured to direct the implementation data store to store the data using a data storage system. The one or more processors are configured to apply evaluation rules to one or more sets of the data in the implementation data store. The evaluation rules are applied to the one or more sets of the data by the one or more processors running previously created scripts of commands of the management system. The one or more processors are configured to determine a deviation measure for at least one of the sets of the data based on the evaluation rules applied to the one or more sets of the data. The one or more processors are configured to present the deviation measure and a restricted list of defined validation decisions for the one or more sets of the data to the analyst. The one or more processors also are configured to receive a selected validation decision in the restricted list from the analyst. The one or more processors also are configured to one or more of validate the one or more sets of the data for use in the action plan, reject the one or more sets of the data for use in the action plan, or identify the one or more sets of the data as requiring additional analysis before validating the one or more sets of the data for use in the action plan.

Optionally, the one or more processors are configured to present the deviation measure and receive the selected validation decision from the analyst having one or more of a training level or an experience level below a designated level associated with writing the previously created scripts of the commands.

Optionally, the data includes one or more of electronic medical record (EMR) encounter data, medical claim data, pharmacy claim data, lab result data, or medical metric data for at least one patient.

Optionally, the one or more production data sources include one or more databases at one or more medical offices, medical clinics, pharmacies, or laboratories.

Optionally, the implementation data store is configured to directly receive the data from the one or more production data sources without modification of the data.

Optionally, the system also includes an intermediate computer server configured to receive the data from the one or more production data sources prior to sending the data to the implementation data store. The intermediate computer server can be configured to modify one or more portions of the data within the intermediate computer server to one or more of normalize or conform the data to one or more requirements of the data storage system.

Optionally, the one or more processors are configured to apply the evaluation rules to the one or more sets of the data and present the deviation measure to the analyst without revealing protected information to the analyst.

Optionally, the one or more processors are configured to automatically apply the evaluation rules to the one or more sets of the data based on a designated schedule.

Optionally, the one or more processors are configured to determine when one or more data-loading events occur as the data is received at the implementation data store. The one or more processors also are configured to automatically apply the evaluation rules to the one or more sets of the data based on occurrence of at least one of the data-loading events.

Optionally, the restricted list of defined validation decisions includes a pass decision indicating that the deviation measure of the one or more sets of the data conformed to a limit, a fail decision indicating that the deviation measure did not conform to the limit, or an indeterminate decision indicating that the analyst was unable to determine whether the deviation measure conformed or did not conform to the limit.

Optionally, the one or more processors are configured to (a) receive identifying data based on input provided by the analyst responsive to receiving one or more of the fail decision or the indeterminate decision and (b) append the identifying data to the one or more sets of the data. The identifying data can represent one or more of the evaluation rules applied to the one or more sets of the data and/or a proposed solution operation to be used to modify the one or more sets of the data or upcoming data to avoid the fail decision on the one or more sets of the data or the upcoming data.

Optionally, the one or more processors are configured to associate evaluation rule data with the one or more sets of the data responsive to rejecting the one or more sets of the data and to communicate an identifier of the one or more sets of the data to a higher-level reviewer responsive to rejecting the one or more sets of the data. The higher-level reviewer has one or more of a training level or an experience level above the designated level associated with writing the previously created scripts.

Optionally, the one or more processors are configured to direct the implementation data store to stop loading of one or more additional sets of the data from a first production data source of the one or more production data sources responsive to rejecting the one or more sets of the data. The first production data source can be associated with the one or more sets of the data that were rejected.

Optionally, the one or more sets of the data are used in a health plan to determine one or more additional medical treatment operations to perform in connection with the at least one patient responsive to validating the one or more sets of the medical data for use in the health plan.

In one embodiment, a tangible and non-transitory computer readable storage medium is provided that includes one or more sets of instructions. This storage medium can be represented by one or more of the scripts described above. These instructions can be implemented using one or more processors to direct the one or more processors to receive data at an implementation data store from one or more production data sources via one or more computerized communication networks, direct storage of the data in the implementation data store using a data storage system, and apply applying evaluation rules to one or more sets of the data in the implementation data store. The evaluation rules are applied to the one or more sets of the data by running previously created scripts of commands of the data storage system. Applying the evaluation rules to the one or more sets of the data outputs a deviation measure for at least one of the sets of the data. The instructions also direct the processor(s) to direct presentation of the deviation measure to an analyst of the deviation measure and a restricted list of defined validation decisions for the one or more sets of the data, receive a selected validation decision in the restricted list from the analyst, and one or more of validate the one or more sets of the data for use in the action plan, reject the one or more sets of the data for use in the action plan, or identify the one or more sets of the data as requiring additional analysis before validating the one or more sets of the data for use in the action plan.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims. The various embodiments are not limited to the arrangements and instrumentality shown in the drawings.

Since certain changes may be made in the above-described systems and methods without departing from the spirit and scope of the inventive subject matter herein involved, it is intended that all the subject matter of the above description or shown in the accompanying drawings shall be interpreted merely as examples illustrating the inventive concept herein and shall not be construed as limiting the inventive subject matter.

What is claimed is:

1. A method for validating data for use in one or more of tracking or generating an action plan, the method comprising:
   receiving the data at an implementation data store from one or more production data sources via one or more computerized communication networks;
   storing the data in the implementation data store using a data storage system;
   applying evaluation rules to one or more sets of the data in the implementation data store, the evaluation rules applied to the one or more sets of the data by running previously created scripts of commands of the data storage system, wherein applying the evaluation rules to the one or more sets of the data outputs a deviation measure for at least one of the sets of the data, the deviation measure indicating whether the one or more sets of the data are legitimately entered with contents of the data being intentionally set to accurate values or whether the one or more sets of the data are invalid with the contents of the data being unintentionally set to inaccurate values;
   presenting, to an analyst, the deviation measure and a restricted list of defined validation decisions for the one or more sets of the data;
   receiving a selected validation decision in the restricted list from the analyst; and
   one or more of validating the one or more sets of the data for use in the action plan, rejecting the one or more sets of the data for use in the action plan, or identifying the one or more sets of the data as requiring additional analysis before validating the one or more sets of the data for use in the action plan.

2. The method of claim 1, wherein the data storage system is one or more of a relational data storage system, a document storage system, or an object database system.

3. The method of claim 1, wherein the analyst is a human being.

4. The method of claim 1, wherein the analyst is an artificial intelligence computerized system.

5. The method of claim 1, wherein the selected validation decision is received from the analyst having one or more of a training level or an experience level below a designated level associated with writing the previously created scripts of the commands.

6. The method of claim 1, wherein the data includes one or more of demographic data, electronic medical record (EMR) encounter data, medical claim data, pharmacy claim data, lab result data, medical metric data, admit data, discharge data, or transfer data for at least one patient.

7. The method of claim 1, wherein the one or more production data sources include one or more databases at one or more medical offices, medical clinics, pharmacies, laboratories, educational entities, or financial institutions.

8. The method of claim 1, wherein the data is directly received at the implementation data store from the one or more production data sources without modification of the data.

9. The method of claim 1, further comprising
changing one or more portions of the data within the intermediate computer server to one or more of normalize or conform the data to one or more requirements of the data storage system.

10. The method of claim 1, wherein the evaluation rules are applied to the one or more sets of the data and the deviation measure is presented to the analyst without revealing protected information in the data to the analyst.

11. The method of claim 1, wherein applying the evaluation rules to the one or more sets of the data automatically occurs based on a designated schedule.

12. The method of claim 1, further comprising:
determining when one or more data-loading events occur as the data is received at the implementation data store, wherein applying the evaluation rules to the one or more sets of the data automatically occurs based on occurrence of at least one of the data-loading events.

13. The method of claim 1, wherein the restricted list of defined validation decisions includes a pass decision indicating that the deviation measure of the one or more sets of the data conformed to a limit, a fail decision indicating that the deviation measure did not conform to the limit, or an indeterminate decision indicating that the analyst was unable to determine whether the deviation measure conformed or did not conform to the limit.

14. The method of claim 13, further comprising:
responsive to receiving one or more of the fail decision or the indeterminate decision, receiving identifying data to be appended to the one or more sets of the data based on input provided by the analyst, the identifying data representing one or more of:
the evaluation rules applied to the one or more sets of the data, or
a proposed solution operation to be used to modify the one or more sets of the data or upcoming data to avoid the fail decision on the one or more sets of the data or the upcoming data.

15. The method of claim 1, further comprising:
associating evaluation rule data with the one or more sets of the data responsive to rejecting the one or more sets of the data; and
communicating an identifier of the one or more sets of the data to a higher-level reviewer responsive to rejecting the one or more sets of the data,
wherein the higher-level reviewer has one or more of a training level or an experience level above a designated level associated with writing the previously created scripts.

16. The method of claim 1, further comprising:
responsive to rejecting the one or more sets of the data, communicating a message that directs a stop to loading of one or more additional sets of the data from a first production data source of the one or more production data sources, wherein the first production data source is associated with the one or more sets of the data that were rejected.

17. The method of claim 1, wherein the one or more sets of the data are used in the action plan to determine one or more additional medical treatment operations to perform in connection with at least one patient responsive to validating the one or more sets of the data for use in the action plan.

18. A data validation system comprising:
an implementation data store configured to receive and store data from one or more production data sources via one or more computerized communication networks, the implementation data store configured to receive the data from the one or more production data sources via an intermediate computer server that modifies one or more portions of the data to one or more of normalize or conform the data to one or more requirements of the data storage system prior to the implementation data store receiving the data; and
one or more processors configured to direct a data storage system to apply evaluation rules to one or more sets of the data in the implementation data store, the evaluation rules applied to the one or more sets of the data by running previously created scripts of commands of the data storage system, wherein applying the evaluation rules to the one or more sets of the data outputs a deviation measure for at least one of the sets of the data, wherein the one or more processors also are configured to direct a user device to present, to an analyst, the deviation measure and a restricted list of defined validation decisions for the one or more sets of the data, the one or more processors also configured to receive a selected validation decision in the restricted list from the analyst and to one or more of validate the one or more sets of the data for use in an action plan, reject the one or more sets of the data for use in the action plan, or identify the one or more sets of the data as requiring additional analysis before validating the one or more sets of the data for use in the action plan.

19. The system of claim 18, wherein the data storage system is one or more of a relational data storage system, a document storage system, or an object database system.

20. A tangible and non-transitory computer readable storage medium comprising one or more sets of instructions that, while implemented, direct one or more processors to:
receive data at an implementation data store from one or more production data sources via one or more computerized communication networks, the data received at the implementation data store from the one or more production data sources via an intermediate computer server that modifies one or more portions of the data to one or more of normalize or conform the data to one or more requirements of the data storage system prior to the implementation data store receiving the data;
store the data in the implementation data store using a data storage system;
apply evaluation rules to one or more sets of the data in the implementation data store, the evaluation rules applied to the one or more sets of the data by running previously created scripts of commands of the data storage system, wherein applying the evaluation rules to the one or more sets of the data outputs a deviation measure for at least one of the sets of the data;
present, to an analyst, the deviation measure and a restricted list of defined validation decisions for the one or more sets of the data;
receive a selected validation decision in the restricted list from the analyst; and
one or more of validate the one or more sets of the data for use in an action plan, reject the one or more sets of the data for use in the action plan, or identify the one or more sets of the data as requiring additional analysis before validating the one or more sets of the data for use in the action plan.

* * * * *